United States Patent [19]

Geithman et al.

[11] Patent Number: 4,755,953
[45] Date of Patent: Jul. 5, 1988

[54] ULTRASONIC TESTING APPARATUS

[75] Inventors: Glenn A. Geithman, Renton; Dennis P. Sarr, Kent, both of Wash.

[73] Assignee: The Boeing Company, Seattle, Wash.

[21] Appl. No.: 815,163

[22] Filed: Dec. 31, 1985

[51] Int. Cl.$^4$ .......................................... G01N 29/04
[52] U.S. Cl. ........................................ 364/507; 73/622; 73/626; 73/628
[58] Field of Search ............... 364/484, 486, 507, 506, 364/552; 73/626, 622, 628, 633, 636, 644

[56] References Cited

U.S. PATENT DOCUMENTS

| | | | |
|---|---|---|---|
| 3,059,228 | 10/1962 | Beck et al. | 340/179 |
| 3,255,417 | 6/1966 | Gottlieb | 328/145 |
| 3,364,466 | 1/1968 | Stine | 340/147 |
| 3,524,162 | 8/1970 | Zill | 340/15.5 |
| 3,585,509 | 6/1971 | Davis et al. | 328/145 |
| 3,649,826 | 3/1972 | Larsson et al. | 235/197 |
| 3,662,274 | 5/1972 | Pritchard et al. | 329/192 |
| 3,704,425 | 11/1972 | Haigh | 328/145 |
| 3,712,989 | 1/1973 | Barton | 307/235 |
| 3,959,732 | 5/1976 | Schaefer | 328/151 |
| 4,102,205 | 7/1978 | Pies et al. | 73/626 |
| 4,173,898 | 11/1979 | Forstermann et al. | 73/611 |
| 4,222,275 | 9/1980 | Sholl et al. | 73/636 |
| 4,241,608 | 12/1980 | Dees et al. | 73/606 |
| 4,327,588 | 5/1982 | North | 364/507 |
| 4,362,995 | 12/1982 | Morris | 328/145 |
| 4,387,597 | 6/1983 | Brandestini | 73/626 |
| 4,392,379 | 7/1983 | Yamaguchi | 73/626 |
| 4,431,007 | 2/1984 | Amazeen et al. | 128/660 |
| 4,462,082 | 7/1984 | Thiele et al. | 73/620 |
| 4,470,304 | 9/1984 | Nusbickel, Jr. et al. | 73/611 |
| 4,635,484 | 1/1987 | Lerch | 73/625 |

Primary Examiner—Parshotam S. Lall
Assistant Examiner—V. N. Trans
Attorney, Agent, or Firm—Finnegan, Henderson, Farabow, Garrett & Dunner

[57] ABSTRACT

An improved ultrasonic inspection system is provided which allows ultrasonic inspection to be performed using either of two ultrasonic frequencies and which also provides improved system sensitivity and dynamic range. In operation, the system produces two signals, one an amplified receive transducer signal and the other an attenuated receive transducer signal. Each signal is converted into a logarithmic representation. The two logarithmic representations are selectively provided to a read-only memory, which operates to output a signal corresponding to the receive transducer signal. Means are also provided which allows the system to use either of two ultrasonic frequencies.

23 Claims, 3 Drawing Sheets

ULTRASONIC TESTING APPARATUS

CROSS REFERENCE TO RELATED APPLICATIONS

The invention is related to the following copending U.S. patent applications assigned to the assignee of the present invention:

DATA RECORDING APPARATUS FOR AN ULTRASONIC INSPECTION SYSTEM, Ser. No. 06/815,050, filed on Dec. 31, 1985 by D.P. Sarr;

ULTRASONIC INSPECTION SYSTEM WITH LINEAR TRANSDUCER ARRAY, Ser. No. 06/815,047, filed on Dec. 31, 1985 by D.P. Sarr and F.D. Young;

ULTRASONIC INSTRUMENTATION FOR EXAMINATION OF VARIABLE-THICKNESS OBJECTS, Ser. No. 06/815,038, filed on Dec. 31, 1985 by D.P. Sarr;

ULTRASONIC INSPECTION SYSTEM WITH MULTIPLEXED MULTIPLE TRANSDUCER RECEIVER, Ser. No. 06/815,048, filed Dec. 31, 1985 by D.P. Sarr;

ULTRASONIC TRANSDUCER WITH SHAPED BEAM INTENSITY PROFILE, Ser. No. 06/815,162, filed Dec. 31, 1985 by G.A. Geithman and D.H. Gilbert; and ULTRASONIC 64 CHANNEL INSPECTION SYSTEM WITH MULTIGATE/MULTI MODE SELECTION, SOFTWARE CONFIGURABILITY, Ser. No. 06/815,044, filed Dec. 31, 1985 by D.P. Sarr.

BACKGROUND OF THE INVENTION

The present invention relates to ultrasonic inspection apparatus and, more particularly, to electronic circuitry for such apparatus.

The ultrasonic inspection of objects is frequently employed in the aircraft manufacturing industry to determine whether those objects have internal defects, such as voids or cracks, which are not apparent from an external inspection of the object. It is necessary to determine whether such defects exist because they could lead to an unexpected structural failure of air frame components incorporated into an aircraft.

Numerous systems are known in the prior art which provide a means to ultrasonically scan and analyze an object to determine whether structural defects exist within that object. Certain ones of such prior art systems contain two transducers: a send transducer which couples ultrasonic energy into the object and a receive transducer which detects or receives the ultrasonic energy transmitted through the object and generates a corresponding electrical signal. These prior art systems then analyze the electrical signal generated by the receive transducer to determine if defects exist within the object under test. However, such prior art systems are limited in at least two respects. First, it is difficult to detect some types of small defects within the object because the sensitivity and dynamic range of the system electronics is insufficient. Second, the prior art systems are not capable of operating at more than one ultrasonic frequency. The second limitation was not a major problem for the electronics of prior art systems since ultrasonic transducers could not satisfactorily operate at more than one ultrasonic frequency. However, recent advances in transducer design have resulted in transducers which are capable of operating at more than one frequency. It is desirable to provide apparatus capable of operating at both high and low frequencies, because, while a low frequency is sufficient to detect defects in some types of objects, a high frequency is required to detect smaller defects and to inspect thinner objects. Therefore, it is desirable to provide an ultrasonic scanning system capable of operating at more than one ultrasonic frequency with increased sensitivity and dynamic range.

SUMMARY OF THE INVENTION

In accordance with the principles of the present invention, a multi-frequency ultrasonic inspection system with increased sensitivity and dynamic range is provided to better enable the operator of the system to detect small defects within a variety of types of articles being tested.

In the present invention, an electrical signal from a receive transducer is supplied to two parallel amplifier circuits. In the first amplifier circuit, the signal is amplified by 45 dB. In the second amplifier circuit, the signal is attenuated by 20 dB. The output signals from the two amplifier circuits are then supplied to two identical logarithmic amplifiers, each of which operates to produce an output signal which represents the logarithm of its input signal. These two logarithmically compressed signals are then supplied to sample and hold circuits which detect and hold the peak value of each logarithmically compressed signal. The signals are then converted to digital signals, and one of the digital representations of the two peak signals supplied to the input terminals of a programmable read only memory (PROM). The PROM is programmed to output a signal which corresponds to the signal generated by the receive transducer.

Means are also provided in the system for allowing the operator to choose between one of two ultrasonic frequencies to be used during the inspection procedure. This improved ultrasonic inspection system is capable of responding to signals from the receive transducer which vary in magnitude from 5 micro-volts peak-to-peak to 50 volts peak-to-peak (Vpp), a range of 140 dB (10 million to 1), with an accuracy of ±1 dB.

To achieve the objects and in accordance with the purposes of this invention, as embodied and broadly described herein, the apparatus of this invention adapted to receive an electrical signal from an ultrasonic receive transducer comprises a plurality of means for supplying a function signal, each of said function signals being a different function of said electrical signal; comparator means responsive to the value of said electrical signal for generating a selection signal; means for generating an output signal representative of an input signal; and means responsive to said selection signal for selectively supplying one of said function signals as an input signal to said generating means, whereby said generating means generates an output signal proportional to said electrical signal over a wide dynamic range.

Still other objects of the invention will be apparent to one skilled in the art from the drawings, which are included as a part of this application, and the following detailed description of the preferred embodiments of the invention.

DESCRIPTION OF THE PREFERRED EMBODIMENT

Figure 1:
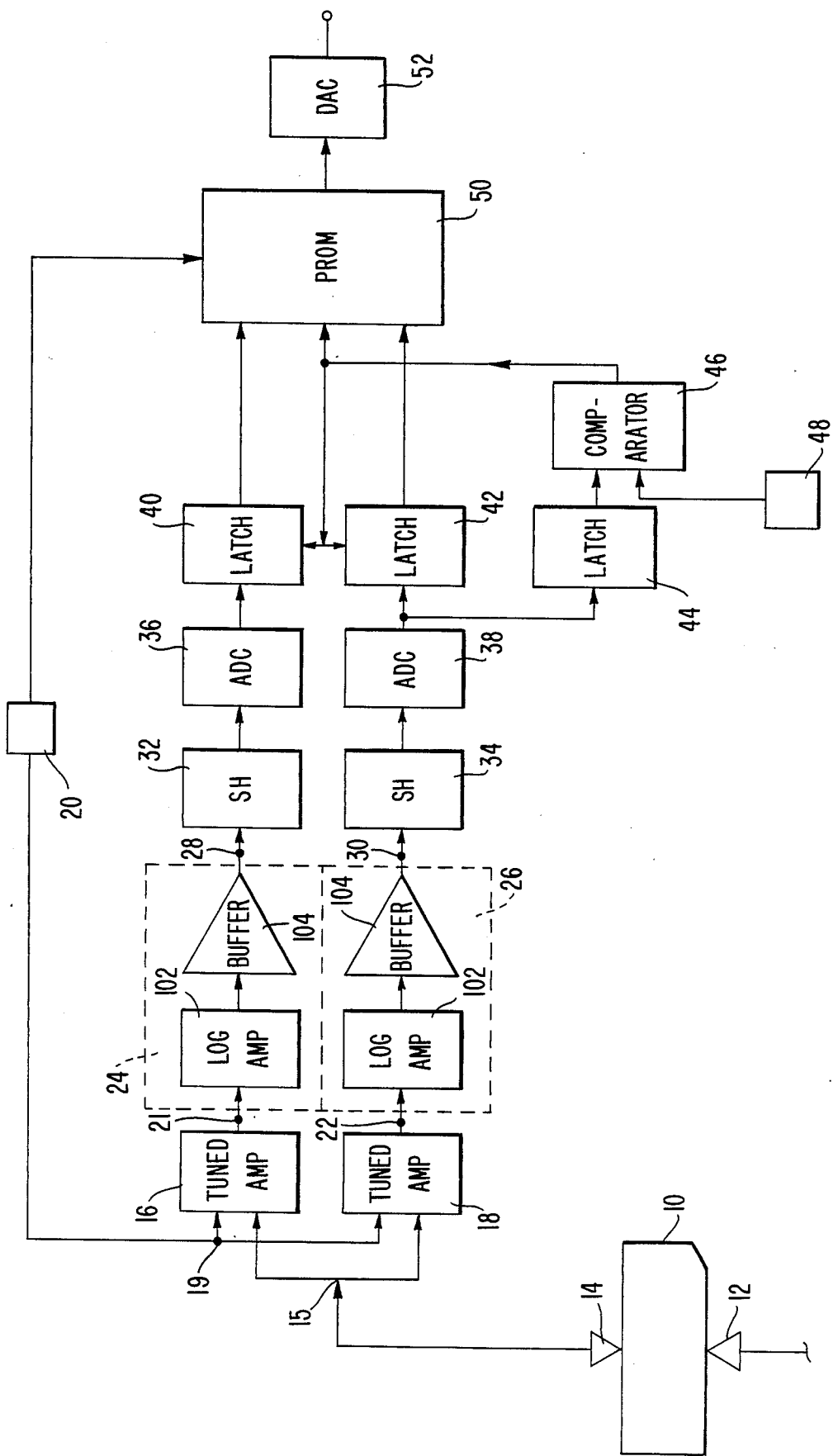
FIG. 1 is a block diagram of a preferred embodiment of an improved ultrasonic inspection system constructed according to the invention.

Referring now to the drawings, in which like reference characters refer to corresponding characters, there is shown in Figure 1 a block diagram of an improved ultrasonic inspection system incorporating a preferred embodiment of the present invention. In FIG. 1, a portion of an object, or workpiece, 10 being tested is located between two ultrasonic transducers 12 and 14, one used for transmitting ultrasonic energy pulses into workpiece 10 and referred to herein as transmit transducer 12, and the other used for receiving the ultrasonic energy pulses which have traveled through the workpiece and referred to herein as receive transducer 14. The amplitude of the ultrasonic energy pulses transmitted through workpiece 10 is monitored by receive transducer 14 and converted by it into a corresponding analog electrical signal, which may vary from 5 microvolts peak-to-peak to 50 volts peak-to-peak.

The analog signal produced by receive transducer 14 is supplied to a common input terminal 15 of dual tuned amplifier circuits 16 and 18 which are capable of operating at either of two ultrasonic frequencies in response to a signal received at a terminal 19 from a switch 20, which is set by the operator. As will be later described in more detail, dual tuned amplifier circuits 16 and 18 each produce an output signal. The output signal of tuned amplifier 16 is the signal received from the receive transducer amplified by 45 dB. The output signal of tuned amplifier 18 is the signal received from the receive transducer attenuated by 20 dB. The amplified signal appears at output terminal 21 of tuned amplifier circuit 16, while the attenuated signal appears at output terminal 22 of tuned amplifier circuit 18. The amplification and attenuation by 45 dB and −20 dB, respectively, are merely illustrative of the preferred embodiment disclosed herein. Other values may be chosen according to the requirements of the particular application, as long as tuned amplifiers 16 and 18 each produce a signal representative of the signal produced by receive transducer 14 and have different gain factors.

The signals which appear at output terminals 21 and 22 of tuned amplifiers 16 and 18 are supplied to two identical logarithmic amplifier circuits 24 and 26 each containing logarithmic amplifiers 102 and buffer circuits 104. Logarithmic amplifier circuits 24 and 26 generate output signals at terminals 28 and 30 which are equivalent to the logarithms of input signals present at terminals 21 and 22, respectively. These output signals vary from 0 to 1 volt peak-to-peak. Therefore, as one skilled in the art will appreciate, the output signal which appears at terminal 28 of logarithmic amplifier circuit 24 represents the logarithm of the output signal of the receive transducer amplified 45 dB, while the signal which appears at output terminal 30 of logarithmic amplifier circuit 26 represents the logarithm of the output signal of the receive transducer attenuated 20 dB.

The invention thus includes a plurality of means for supplying a function signal, each of said function signals being a different function of the electrical signal. As can be seen in FIG. 1, tuned amplifiers 16 and 18 and logarithmic amplifier circuits 24 and 26 respectively combine to produce signals at terminals 28 and 30 which are the logarithms of two signals, one of which is equal to the analog electrical signal produced by transducer 14 amplified by 45 db and the other of which is equal to the analog electrical signals produced by transducer 14 attenuated by 20 db, respectively.

These two logarithmic signals are supplied to identical gated sample and hold circuits (SH) 32 and 34 which detect the peak value of each signal for a given period of time and hold that peak value. Those peak values are then converted into digital signals by analog-to-digital converters (ADC) 36 and 38. The digital output signal of ADC 36 which represents the amplified receive transducer signal is held for a period of time in a latch circuit 40, while the digital output signal of ADC 38 which represents the attenuated receive transducer signal is held for a period of time in latch circuits 42 and 44. The invention thus includes comparator means responsive to the value of the electrical signal for generating a selection signal as embodied herein. A comparator 46 is provided for comparing the output of latch circuit 44, which is the digital representation of the attenuated signal, to a preset minimum value selected by the system operator through a switch 48. When the digital representation of the attenuated signal increases above the operator-selected minimum value, the output of comparator 46 changes state.

The output of comparator 46 is supplied to latch circuits 40 and 42 and to means generating an output signal from an input signal. As embodied herein and as shown in FIG. 1, the generating means includes a programmable read-only memory (PROM) 50. The output of comparator 46 is thus supplied as address inputs to PROM 50. When the attenuated signal is below the operator-selected minimum value, latches 40 and 42, in response to the output of comparator 46, cause the digital representation of the amplified receive transducer signal to be provided from latch 40 to PROM 50. However, when the attenuated signal is above the minimum level, the output of comparator means 44 changes state and latches 40 and 42, in response to the change in state of the output of comparator 46, cause the digital representation of the attenuated receive transducer signal to be provided from latch 42 to PROM 50.

Latches 40 and 42 thus constitute means responsive to the output of comparator 46 acting as a selection signal for selectively supplying one of the function signals as an input signal to the generating means.

PROM 50 functions as a look-up table. As will be described later in detail, PROM 50 is programmed to contain data which corresponds to various output signals of the receive transducer at each of two ultrasonic frequencies. The signals which are supplied as address inputs to PROM 50 represent the logarithm of either the amplified or attenuated signal received from the receive transducer.

PROM 50 is programmed so that when it receives an address input signal, it determines whether that address input represents the amplified or the attenuated signal, based upon the state of comparator 46 output. In addition, PROM 50 receives a signal from switch 20 which indicates which of the two ultrasonic frequencies have been selected by the operator, thus allowing PROM 48 to select the appropriate output data representative of the receive transducer signal.

The output signal of PROM 50 is converted by a digital-toanalog converter (DAC) 52 into an analog signal, which varies from 0 to 10 Vpp, which is then supplied to additional circuitry (not part of the present invention) for analysis and display.

Figure 2:
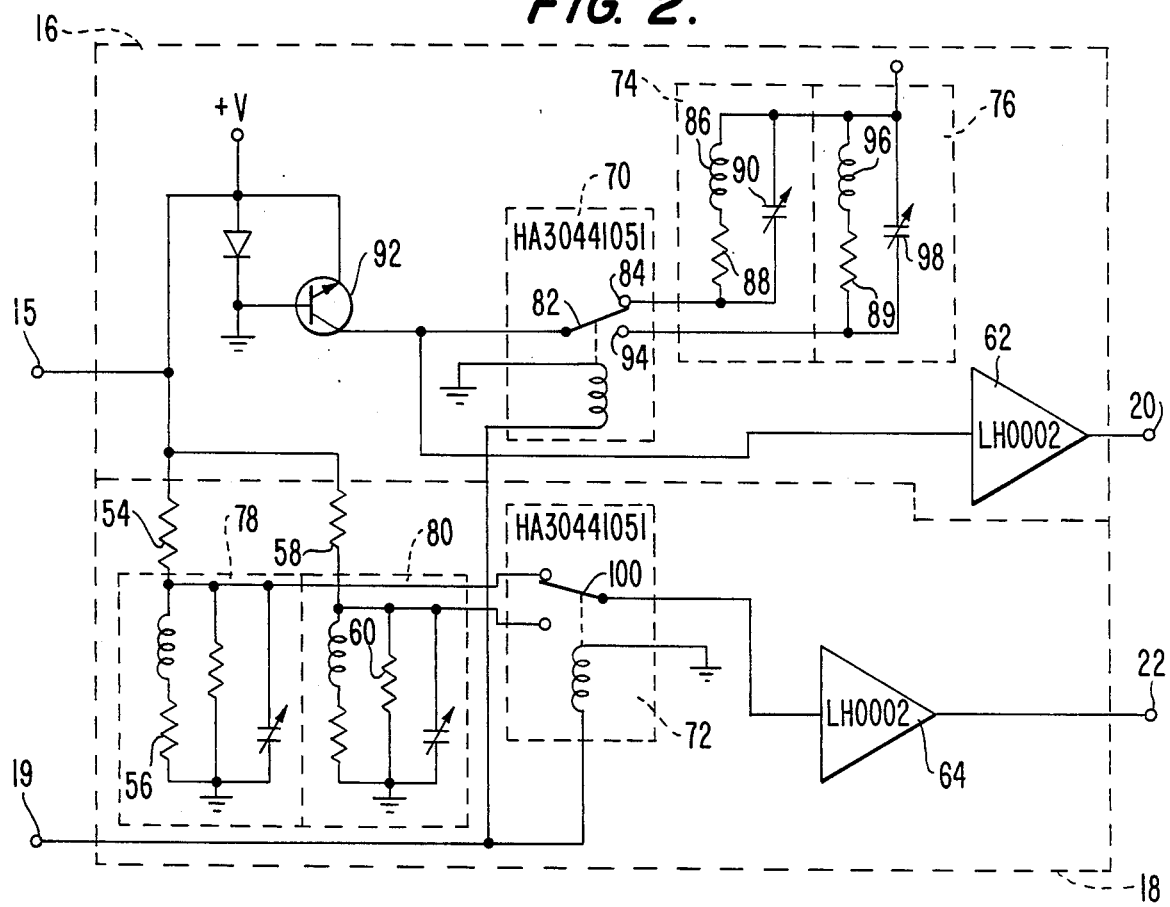
FIG. 2 is a detailed circuit diagram of the initial amplifier stage of the system of FIG. 1.

Referring now to FIG. 2, dual tuned amplifier circuits 16 and 18 are shown in greater detail. Since the operation of the components of tuned amplifiers 16 and 18 is well-known, such components are shown in FIG. 2 but will not be described. The output signal of the receive transducer is provided to input terminal 15. The signal is then provided to two tuned amplifier circuits, 16 and 18. Amplifier circuit 16 provides 45 dB amplification to the signal through the operation of transistor 92 and associated circuitry. Amplifier circuit 18 operates to provide −20 dB attenuation to the signal through the operation of resistors 54, 56, 58, and 60.

Both the amplified signal and the attenuated signal are supplied to identical buffer circuits 62 and 64 which provide output signals to output terminals 20 and 22 of the dual tuned amplifier circuits.

The capability of switching from a first to a second ultrasonic frequency is provided by switching circuits 70 and 72. These switching circuits operate to select one of two tuned circuits 74, 76 and 78, 80 in each tuned amplifier circuit in response to a signal from switch 20, which is supplied to terminal 19. Referring first to the amplifier circuit 16 shown in detail in the top portion of FIG. 2, when switch contact 82, which operates in response to the signal received from switch 20, touches contact 84, tuned circuit 74 consisting of inductor 86, resistor 88, and variable capacitor 90 is connected into the collector circuit of transistor 92 of tuned amplifier 16. When switch contact 20 is touching contact 94, tuned circuit 76 consisting of inductor 96, resistor 89, and variable capacitor 98 is switched into collector circuit of transistor 92.

Switch contact 100 operates in a similar manner in amplifier circuit 18 shown in detail in the bottom portion of FIG. 2, to associate either tuned circuit 78 or tuned circuit 80 with the circuit of tuned amplifier 18. Both switch contact 82 and switch 100 are controlled by a signal provided at terminal 19, which is generated by switch 20 in response to the system operator selecting one or the other of the two ultrasonic frequencies. Therefore, the above described circuit provides means by which the dual tuned amplifier circuit will operate using one of two ultrasonic frequencies selected by the operator.

Referring back to FIG. 1, the operation of dual logarithmic amplifiers 24 and 26 will be explained. The signals which appear on output terminals 21 and 22 of amplifier circuits 16 and 18 are connected to input terminals 21 and 22, respectively, of identical logarithmic amplifier devices 102. Devices 102 are standard components which may be ordered from Electronic Countermeasures, Inc. under the product designation CMO-12. Each of logarithmic amplifier devices 102 operate to generate an output signal which represents the logarithm of its input signal.

The outputs of the logarithmic amplifier devices 102 are supplied to identical buffer circuits 104 which serve to condition and smooth the signals. Buffer circuits 104 are of conventional construction and are known by the commercial designation LH0002. The outputs of buffer circuits 104 are provided at terminals 28 and 30. As one skilled in the art will understand, the output signal which appears at output terminal 28 represents the logarithm of the signal received from the receive transducer amplified by 45 dB, while the output signal provided an output terminal 30 represents the logarithm of the signal received by the received transducer attenuated by -20 dB. This can be seen in FIG. 3, which is a graph showing the output signal of logarithmic amplifiers 24 and 26 on the y-axis and the value of the receive transducer signal on the x-axis. Curve M represents the output of logarithmic amplifier 24, which receives the amplified receive transducer output signal. Curve N represents the output of logarithmic amplifier 26, which receives the attenuated receive transducer output signal. The output signal which appears at terminal 28 is represented by curve M, while the output signal which appears at terminal 30 is represented by curve N.

Figure 4:
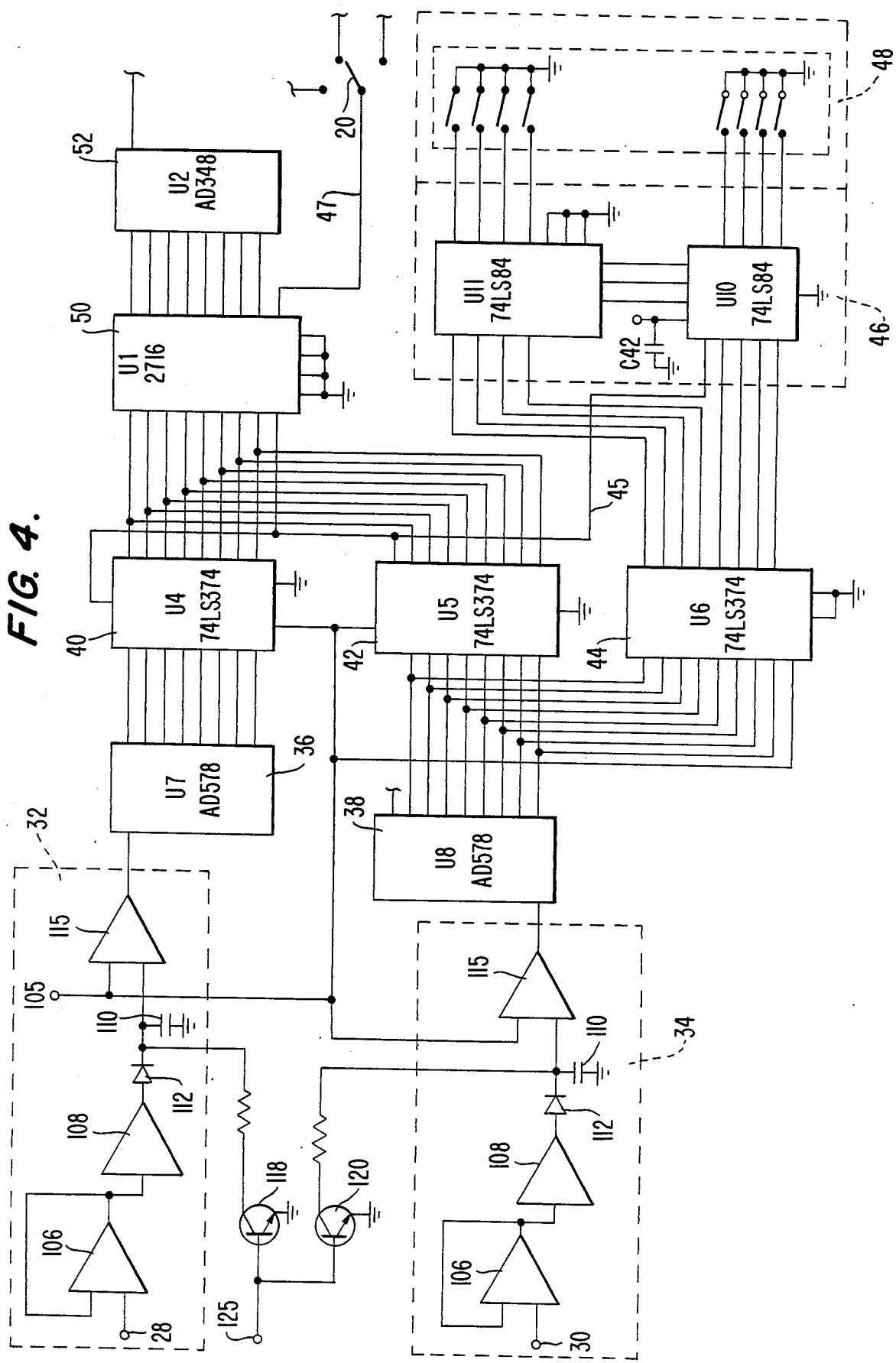
FIG. 4 is a detailed diagram showing the analog-to-digital converters, latching circuits, PROM circuit, and digital-to-analog converter of the system of FIG. 1.

Referring now to FIG. 4, the signals which appear at output terminals 28 and 30 of the logarithmic amplifier circuits 24 and 26 are provided to two peak sample and hold circuits 32 and 34. Sample and hold circuits 32 and 34 are of conventional construction and operate to detect the peak value of the signal generated by each logarithimic amplifier and to hold that peak value for a certain period of time determined by the system. A system timing signal is provided on terminal 105, which serves to synchronize the receive transducer electronics with the pulses transmitted by transmit transducer 12. The control circuitry which generates the timing signal is described in the aforementioned U.S. Pat. Application Ser. No 06/814,044 filed Dec. 31, 1985 by Dennis P. Sarr, the disclosure of which has been incorporated by reference. Peak sample and hold circuits 32 and 34 each consist of a high-speed peak detector incorporating a fast operational amplifier 106, a buffer circuit 108 which charges a 100 pf capacitor 110 through a hot carrier diode 112, and a lowspeed sample and hold circuit 115. In operation, capacitors 110 are charged to a voltage which corresponds to the peak value of each logarithically compressed signal. Low speed sample and hold circuits 115 acquire and hold the value of each peak voltage. Capacitors 110 are then reset using bipolar transistors 118 and 120, which are triggered by a timing pulse applied to terminal 125 by associated control circuitry. The control circuitry is described more completely in copending U.S. Pat. Application Ser. No. 06/814,044 filed by Dennis P. Sarr, the disclosure of which is hereby expressly incorporated by reference, and thus is not shown in FIG. 4.

The value held in each sample and hold circuit 32 and 34 is then converted into a digital signal by, analog-to-digital converters 36 and 38 and provided to latch circuits 40, 42, and 44. These are all standard components well known in the art. For example, the analog-to-digital converters are known by the product designation AD570, and the latch circuits are known by the product designation 74LS374.

As shown in FIG. 4, the digital signal from analog-to-digital converter 38, which represents the attenuated receive transducer signal, is supplied through latch circuit 44 to comparator circuit 46, where its value is compared to a preset value selected by the system operator by switch 48. When the value of the attenuated signal exceeds the value preset by switch 48, an output signal is generated by the comparator 46. The comparator output signal is supplied over line 45 to latch circuits 40 and 42.

As shown FIG. 4, PROM 50 is connected to latch circuits 40 and 42, which hold the amplified and the attenuated receive transducer signal, respectively. When the signal from receive transducer 14 is less than the preset value established by switch 48, latch circuit 42 will be disabled through operation of the comparator 46 output signal and PROM 50 will receive only the signal from latch circuit 40, which represents the amplified receive transducer output.

However, when the value of the attenuated signal increases above the operator-selected minimum value, the output of comparator 46 changes state, which disables latch circuit 40 and enables latch circuit 42. The PROM 50 then receives the output signal from latch circuit 42, which represents the attenuated receive tranducer signal.

Therefore, the PROM 50 receives a digital representation of the amplified receive transducer signal until the receive transducer signal increases above a certain level. Then, means are provided to automatically switch PROM 50 to receive the attenuated receive transducer signal. Moreover, the comparator output signal on line 45 is supplied to PROM 50 as an address input bit to select the proper block of output data of PROM 50. The selection of the proper block of data corresponding to the selected frequency of operation is provided by another address input bit supplied by a line 47 from switch 20.

The operation of the above described switching system can be better understood by referring again to FIG. 3. As is evident from FIG. 3, the output of the logarithmic amplifier 24, shown by curve M, increases from 0 to approximately 1 volt as the received transducer signal increases from one microvolt or $10^{-6}$ volts, up to $10^{-2}$ volts, indicated at 130. At that point, logarithimic amplifier 24 oegins to saturate. However, beginning at the same point 130, that is, when the receive transducer output signal is at $10^{-2}$ volts, the output of logarithmic amplifier 26 shown by curve N, begins to increase from 0 volts at approximately the same input level which causes logarithmic amplifier 24 to saturate. As is evident from FIG. 3, the output signal of logarithmic amplifier 26 increases from 0 to 1 volt as the receive transducer signal increases from $10^{-2}$ volts up to 100 volts, at which point (indicated at 135) logarithmic amplifier 26 reaches its saturation point. Therefore, as is clear from FIG. 3, by setting switch 48 at a value indicated at 130 in FIG. 3, the switched combination of the output signals of two logarithmic amplifiers 24 and 26, one operating in response to the amplified receive transducer signal and second operating response to the attenuated receive transducer signal, provides the capability of having a system which is both accurate and responsive over a wide dynamic range.

Figure 3:
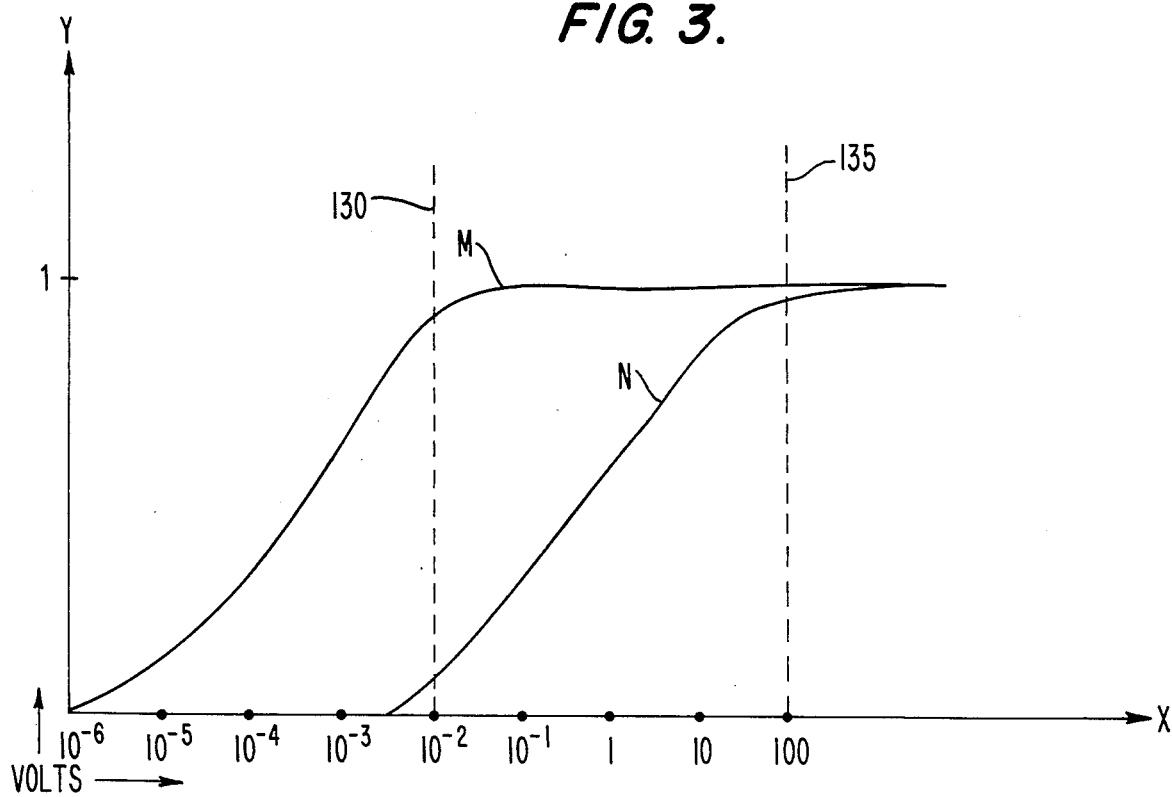
FIG. 3 is a graph showing the output signals of the two logarithmic amplifier circuits of the system of FIG. 1.

The point at which latch circuit 40 is disabled and no longer feeds data into PROM 50 is selected by the operator by simply setting a pre-determined value into switch 48. That value constitutes the minimum level which is provided to the comparator, as discussed above. Therefore, the operator has flexibility in determining at which point the system will switch from one logarithmic amplifier circuit output to the other. For the described embodiment, that switching point is set to occur when the receive transducer signal approaches $10^{-2}$, volts as shown in FIG. 3.

Returning now to FIG. 4, the operation of PROM 50 will be explained. PROM 50 is programmed with data which represents possible values of the receive transducer signal, when either of two ultrasonic frequencies are used. As described above, the input, or address, signals to the PROM 50 represent the logarithm of either the amplified or attenuated receive transducer output signal. The PROM memory is thus divided into two blocks of two subblocks each. One block contains data which correspond to the amplified signal at each of the two ultrasonic frequencies, while the other block contains data which corresponds to the attenuated signal at each of the two resonant frequencies. As described above, when the attenuated logarithmic signal is at or near 0, the output of the comparator 46 is at a low level, which disables latch 42 and allows latch circuit 40 to provide a partial address input to PROM 50. The remainder of the address information, which selects the proper section, is provided by line 45 from comparator 46 and line 47 from switch 20. In response to that address input data, the PROM 50 outputs a digital signal which corresponds to the receive transducer output signal.

When the logarithmic signal which represents the attenuated receive transducer output signal increases above the operator selected minimum value, the output of comparator 46 on line 45 changes to a high level. This output is provided to latch circuits 40 and 42 and to PROM 50. In response to the output, latch circuit 40 is disabled and the PROM receives data from latch circuit 42, which represents the attenuated signal. The comparator output signal also serves as an additional address data bit input to PROM 50 over line 45, which causes PROM 50 to output data from its second section, which contains data corresponding to the attenuated signal.

As described above, when the system operator selects a second ultrasonic frequency for inspection purposes, a signal is provided from switch 20 over line 47 to PROM 50, which causes data which corresponds to the second ultrasonic frequency to be output from PROM 50.

PROM 50 is programmed as follows. A calibrated input signal is fed into the system at terminal 15. The digital representation of that signal which is generated by the system and provided to the input of PROM 50 as an address is noted. The value of the calibrated input signal is then stored in PROM 50 at the address location which corresponds to the digital representation provided to PROM 50. Therefore, in operation, when PROM 50 receives that same digital signal from the system as an address, it will output the value stored at that address, which will correspond to the receive transducer signal corrected for any nonlinearities present in components 16, 18, 24, 26, 32, 34, 36, and 38. These steps are repeated at 5 dB steps over the range of possible receive transducer signals for each of the two ultrasonic frequencies to be employed. A computer then interpolates between steps and fills PROM 50 with the appropriate data.

Therefore, as will be understood by one skilled in the art, a system having high sensitivity and wide dynamic range has been provided by this invention whereby a signal output from a receive transducer of an ultrasonic inspection system, which varies up to a 140 dB, is logarithmicaliy compressed by a two-stage amplifier system for processing and then reconstructed into the original signal by use of a programmable read-only memory. Other means for achieving the objects of this invention, without departing from the teachings and spirit of this invention, will be obvious to one of ordinary skill in the art.

What is claimed is:

1. An ultrasonic inspection apparatus, comprising:
   a transducer for receiving an ultrasonic inspection signal and for producing an electrical signal;
   a plurality of means for processing said electrical signal; a like number of logarithm means for producing logarithmic representations of the outputs of said processing means;
   comparator means for generating a selection signal in response to the value of said electrical signal; and
   memory means for generating an output signal which is representative of said electrical signal; said memory means generating said output signal using a selected one of said logarithmic representations in response to said selection signal.

2. Apparatus as recited in claim 1 wherein said plurality of processing means comprises a first circuit which receives and amplifies said first output signal and a second circuit which receives and attenuates said first output signal, and said selection signal comprises a digital signal representative of the relationship between said electrical signal and a predetermined reference level.

3. Apparatus as recited in claim 2 wherein said memory means comprises:
   a memory device including address inputs, data outputs, a first set of stored data values representative of corrected values of said electrical signal below said reference level, and a second set of stored data values representative of corrected values of said electrical signal above said reference level; said logarithm means being connected to said address inputs, and said memory device selectively providing an output signal from said first and second sets of stored data in response to the value of said selection signal; and
   a digital-to-analog converter connected to the output of said memory device.

4. Apparatus as recited in claim 3, wherein said first and second circuits are each tuned amplifier circuits responsive to either a first or a second ultrasonic frequency in accordance with a frequency selector signal.

5. Apparatus as recited in claim 4 wherein said memory device further includes third and fourth sets of stored data values representative of corrected values of said electrical signal when said second ultrasonic frequency is employed, said third set of stored data values being representative of corrected values of said electrical signal below said reference level and said fourth set of stored data values being representative of corrected values of electrical said signal above said reference level.

6. Apparatus as recited in claim 1 wherein said comparator means comprises sample and hold circuits connected to said logarithm means.

7. Apparatus as recited in claim 6 wherein said generating means comprises digital-to-analog converter circuits connected to said sample and hold circuits.

8. Apparatus as recited in claim 7 wherein said generating means comprises latch circuits connected to said digital-to-analog circuits.

9. A method of ultrasonically analyzing an object, comprising:
   transmitting ultrasonic energy through the object;
   receiving the ultrasonic energy which travels through said object;
   generating an electrical signal which represents the ultrasonic energy received;
   producing amplified and attenuated versions of said electrical signal;
   generating logarithmic representations of said amplified and said attenuated versions of said electrical signal;
   selectively supplying the logarithmic representations to a programmed memory; and
   generating an output signal from data stored within said programmed memory which corresponds to said electrical signal.

10. A method as recited in claim 9, wherein said logarithmic representation of said amplified electrical signal is supplied to said programmed memory when said electrical signal is below a predetermined value.

11. A method as recited in claim 9, wherein said logarithmic representation of said attenuated electrical signal is supplied to said programmed memory when said electrical signal is above said predetermined level.

12. An ultrasonic inspection apparatus adapted to receive an electrical signal from an ultrasonic receive transducer, said apparatus comprising:
   a plurality of means for supplying a function signal, each of said function signals being a different function of said electrical signal;
   comparator means responsive to the value of said electrical signal for generating a selection signal;
   memory means for generating an output signal representative of an input signal; and
   latch means responsive to said selection signal for selectively supplying one of said function signals as an input signal to said generating means, whereby said generating means generates an output signal proportional to said electrical signal over a wide dynamic range.

13. Apparatus as recited in claim 12, wherein each of said function signals is equal to the logarithm of a multiple of said electrical signal.

14. Apparatus as recited in claim 13, wherein said output signal generating means comprises a read-only memory.

15. Apparatus as recited in claim 14, wherein said plurality of function signal supplying means comprises first and second circuits respectively supplying first and second signals substantially proportional to said electrical signal, the constant of proportionality of said first circuit being greater than the constant of proportionality of said second circuit.

16. Apparatus as recited in claim 15, wherein the constant of proportionality of said second circuit is less than unity.

17. Apparatus as recited in claim 16, wherein said function signal supplying means comprises first and second logarithmic amplifiers respectively connected to the outputs of said first and second circuits.

18. Apparatus as recited in claim 17, wherein said first and second circuits respectively comprise first and second tuned amplifiers.

19. Apparatus as recited in claim 18 comprising means responsive to an external signal for generating a frequency selection signal and wherein each of said first and second tuned amplifiers comprises first and second tuned circuits respectively responsive to first and second operating frequencies and selectively connected to said tuned circuits in response to said frequency selection signal.

20. Apparatus as recited in claim 19 wherein each of said data sets comprises first and second subsets corresponding to said first and frequencies, and wherein said read-only memory is responsive to said frequency selection signal and said selection signal to supply data from one of said subsets as an output signal.

21. Apparatus as recited in claim 14, wherein said read-only memory comprises a plurality of data sets each corresponding to one of said function signals, and said read-only memory supplies an output signal from a selected one of said data sets in response to said selection signal.

22. Apparatus as recited in claim 14, wherein said means responsive to said selection signal for selectively supplying one of said function signals comprises a plurality of latches.

23. Apparatus as recited in claim 22, wherein one of said latches is connected to each of said means for supplying a function signal.

\* \* \* \* \*